(12) United States Patent
Harada et al.

(10) Patent No.: US 10,413,627 B2
(45) Date of Patent: *Sep. 17, 2019

(54) COMMUNICATING SCALE

(71) Applicant: Vium, Inc., San Mateo, CA (US)

(72) Inventors: Kevin Harada, San Francisco, CA (US); Jonathan Betts-Lacroix, Belmont, CA (US)

(73) Assignee: Vium, Inc., San Mateo, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/396,042

(22) Filed: Dec. 30, 2016

(65) Prior Publication Data

US 2017/0108369 A1   Apr. 20, 2017

Related U.S. Application Data

(63) Continuation-in-part of application No. 14/631,230, filed on Feb. 25, 2015, now Pat. No. 9,671,276.

(51) Int. Cl.
*A01K 1/03* (2006.01)
*G01G 17/08* (2006.01)
(Continued)

(52) U.S. Cl.
CPC ............... *A61L 2/18* (2013.01); *A01K 1/031* (2013.01); *A01K 11/006* (2013.01); *A01K 29/00* (2013.01);
(Continued)

(58) Field of Classification Search
CPC .... G01G 19/52; G01G 21/22; G01G 23/3728; A01K 1/015; A01K 1/031
See application file for complete search history.

(56) References Cited

U.S. PATENT DOCUMENTS 5,895,894 A * 4/1999 Zumbach ............... G01G 21/30
177/124
8,796,565 B2 * 8/2014 Lauer ..................... G01G 21/28
177/243
(Continued)

FOREIGN PATENT DOCUMENTS

JP   H08-178736   *  7/1996   ............. G01G 21/28
JP   2005283328   * 10/2005   ............... G01G 1/24

OTHER PUBLICATIONS

English translation of JP H08-178736.*
English translation of JP 2005283328.*

*Primary Examiner* — Natalie Huls
(74) *Attorney, Agent, or Firm* — Kim Rubin, Patent Agent

(57) ABSTRACT

A communicating sterile scale is described suitable for automated use in animal cages. An upper module provides a weighing platform, electronics, upward facing wireless communication elements, a protecting skirt, and interface to a combined weight-bearing and electrical penetration element. A lower module provides a case, internal electronics, load cell, power source, sterile-sealed flexible complaint membrane and a combined weight bearing and electrical penetration element through the membrane. The upper and lower modules are easily separable for sterilization by immersion in a sterilizing fluid. The power source in the case may be charged through same electrical penetrating element. The membrane comprises a perimeter that is attached and sealed to the case, a penetration area penetrated by the rigid weight-bearing element, and an isolating compliance area. The skirt on upper module protects detritus from entering from below onto the membrane, while providing open-air movement. Upward facing narrow-beam communication elements provide association-free communication protocols.

13 Claims, 1 Drawing Sheet

(51) Int. Cl.
*G01G 21/30* (2006.01)
*G01G 23/37* (2006.01)
*A61L 2/18* (2006.01)
*A01K 29/00* (2006.01)
*A01K 11/00* (2006.01)
*H04Q 9/00* (2006.01)

(52) U.S. Cl.
CPC ............ *G01G 17/08* (2013.01); *G01G 21/30* (2013.01); *G01G 23/3728* (2013.01); *H04Q 9/00* (2013.01); *H04Q 2209/47* (2013.01)

(56) References Cited

U.S. PATENT DOCUMENTS

| | | | |
|---|---|---|---|
| 8,797,166 B2* | 8/2014 | Triener | G01G 17/08 340/573.1 |
| 9,671,276 B1* | 6/2017 | Betts-Lacroix | G01G 21/28 |
| 2012/0085291 A1* | 4/2012 | Conger | A01K 1/0047 119/419 |
| 2014/0251228 A1* | 9/2014 | Jensen-Jarolim | A01K 29/005 119/421 |
| 2016/0069737 A1* | 3/2016 | Canwell | G01G 21/28 177/238 |
| 2016/0231167 A1* | 8/2016 | Masin | G06K 7/10386 |
| 2017/0105385 A1* | 4/2017 | Betts-Lacroix | A01K 1/031 |
| 2017/0108368 A1* | 4/2017 | Harada | G01G 19/00 |
| 2018/0103617 A1* | 4/2018 | Izumo | A01K 29/00 |

\* cited by examiner

COMMUNICATING SCALE

This invention relates to a communicating, wireless scale.

BACKGROUND OF THE INVENTION

Vivariums house a number of animals, typically test animals, such as mice, in a number of cages, often a large number. The test animals are frequently used to test drugs, genetics, animal strains, husbandry practices, methods of treatment, procedures, diagnostics, and the like. We refer to all such uses of a vivarium as a study.

Regular weighing of animals is an important part of studies. In the prior art, weighing is done by hand and is labor intensive. The handling of the animals often changes their behavior or their health, altering the results or quality of the study. Also, handling the animals comprises the sterility of the cages and animals, putting the health of the animals and workers at risk.

Such manual weight recording is inherently infrequent due to the high labor time and cost. This infrequency creates three weakness of the prior art. First, problems may not be discovered until after an unacceptable delay, such as a failure to eat. Second, subtle behavior or health attributes, such as an animal's eating schedule, will be missed. Third, manual handling requires light for the worker. For many animals, this light interferes with and alters their behavior and health, and thus alters the results of the study compared with animals in their natural lighting regimen.

Vivarium cages are normally pathogen-free. Animals and thus their cages must be isolated from outside pathogens or contamination and from pathogens or contamination from other animals or other cages. This presents a significant challenge to vivarium automation and in particular to in-cage animal weighing and automatic animal identification. Electronic equipment placed inside a cage may need to be discarded after a single study due to the inability to sterilize the equipment between studies. Such equipment may be an animal ID sensor, a scale, or a wireless transmitter. In addition, in order to keep the cages pathogen-free it is desirable to have as few cage penetrations as possible. This means that power or data wiring to electronic equipment inside the cage is undesirable. Although this requirement motivates wireless devices, these devices must then be battery powered, which adds to cost, size and weight, and may introduce pathogens. Batteries may have to be changed out during a study, which adds to both equipment and labor costs and may introduce pathogens.

Sterility or pathogen free is important in vivariums to assure the health of the animals and the health of the workers. Also, sterility is critical for accurate, consistent, credible and repeatable study results. Sterility refers to the sufficient restriction of pathogen type and quantity so as to not affect the outcome of the study or the health or the behavior of animals or people. Sterility also refers to husbandry attributes, supplies and usage, as well as health.

An automated scale to meet vivarium requirements must have the following features: electronics in a fully sterile enclosure; animal chew-proof exterior; all components sterilizable by immersion in a sterilizing fluid; internal, rechargeable batteries; wireless connectivity, ideally redundant, ideally narrow range, ideally bi-directional; tool-less assembly and disassembly for sterilization and charging; free of clogging from bedding; reusable in different cages; free of dangerous or poisonous elements to animals; and a cage-mounting configuration to avoid movement by cage animals. Prior art with these features has not been identified.

SUMMARY OF THE INVENTION

In one embodiment a scale comprise an upper module comprising a weighing platform, skirt, electronics and a wireless communication element; and a lower module comprising a case with electronics, a load cell, and power source covered with a sealing, flexible, complaint membrane. The membrane is penetrated by a rigid penetrating element that provides both rigid weight-bearing connectivity from the upper module to the load cell and electrical connections from the electronics in the case to electronics on the upper module.

The case is sealed by the membrane. A perimeter area of the membrane is attached to a perimeter of the case with a sterile seal and optionally by the use of a membrane frame. The membrane comprises three area regions: the perimeter area; a central area that is penetrated by the rigid penetrating element; and a compliance area that isolates the perimeter area from the central area. The penetration is sealed at its penetration. Seals provide sterility, meaning a barrier against pathogens that could harm the animal, cage, cage air, or study results.

The platform skirt surrounds the upper perimeter of the case. The case comprises a load cell or other weight-measuring element; electronics, chargeable power source such as lithium batteries, a processor and communication electronics.

The upper module comprises wireless communication, such as a radio or optical, which may be bi-directional and may be redundant. The antenna or optical element connects to electronics in the case via connections inside the penetrating element. The one or more communications elements may have a narrow beam to avoid interference with other cages and may be elevated to avoid contamination, and may be covered so as to be chew resistant.

The weighing platform and skirt are made from non-poisonous material and are shaped, such as with edge and corner radii, to be chew resistant. The skirt may be dimensioned, configured, and shaped to avoid contamination between the skirt and the case, such as by bedding. The power source in the case may be charged via the same electrical connector that connects the upper and lower modules. The upper module may be removed via a simple mating element to the penetrating element. Mechanical removal of the upper module accomplishes electrical disconnection concurrently. The upper and lower modules are then separately sterilizable by immersion in a sterilizing fluid. Re-attaching the modules accomplishes mechanical connection and electrical connection concurrently. The case comprises peripheral projections or detents to secure it in a fixed cage location. The projections or detents may be configured to mate with a cage so the scale may be placed and removed by hand and held in place by gravity so that no tools or hand-operated fasteners are required.

DETAILED DESCRIPTION OF THE INVENTION

Figure 1:
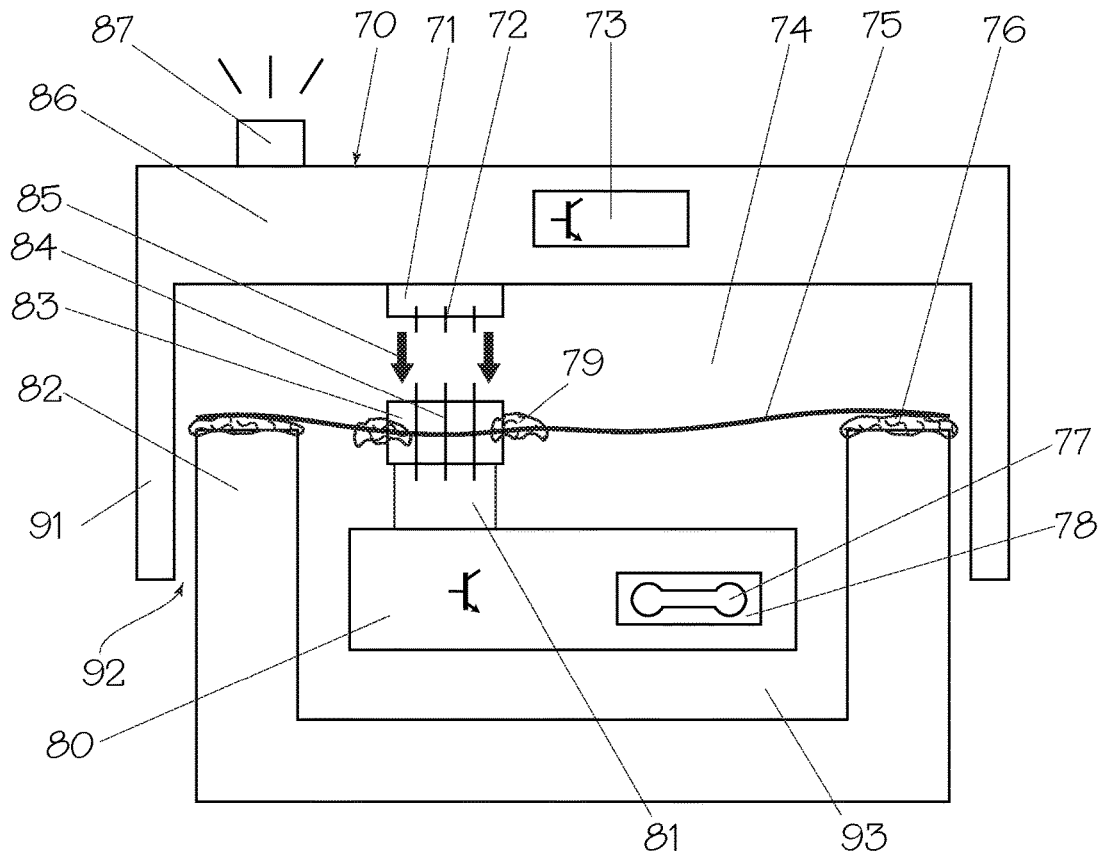
FIG. 1 shows a side view of exemplary upper and lower modules, skirt and penetrating element.

Turning now to FIG. 1, we see a cut-away side view an embodiment. A cut-away view of the case 82 is shown. The case may be rectangular, oval, or another shape. The shape may fit conveniently in a corner or end of an animal cage. The material may be metal, such as stainless or galvanized steel or aluminum, or a plastic such as ABS or another plastic that is non-toxic if chewed and does not out-gas. The case may be injection molded, 3D printed, monolithic or assembled from components.

A cut-away side view of a weighing platform 86 with a skirt 91 is shown. A top surface 70, of an upper module 86, may be considered a weighing platform; or the entire upper module (86 plus attached elements) may be considered a weighing platform. The weighing platform surface 70, upper electronics 73, communication element(s) 87, skirt 91 and mechanical and electrical mating elements 72 are the primary components of the upper module 86. The weighing platform skirt 91 overlaps the upper perimeter of the case 82 creating a vertical opening 92 that is narrow enough and high enough to minimize penetration into the opening of cage detritus such as bedding, yet wide enough to achieve mechanical clearance between the weighing platform and case and also to not collect moisture. The weighing platform clears the membrane and optional membrane frame sufficient for the weighing platform to move or pass pressure through the penetrating element, and to tolerate manufacturing and operational tolerances, age, and distortion, and to avoid accumulation of moisture. Note that pathogens, vapors and aerosols may pass from the interior of a cage housing the scale, through the vertical opening 92, and then between the upper module 86 and the upper surface membrane 75. Such a volume, open to pathogens, is shown 74.

An optional membrane frame is not shown. A membrane frame shape and dimensions are functionally matched to the top perimeter of the case. Typically, the membrane is first attached to the optional frame, and then the frame is attached to the case. In one embodiment, the membrane provides the two functions: (i) sterile seal between the outside of the case and the inside; (ii) high compliance to not adversely affect a measured weight on top of the weighing platform. A rubber or latex sheet may be used. Sterile seals may also or alternatively be provided via grease, calk, glue, adhesive, other gasket material, a pressure fit, and the like. Securing of the membrane to the optional frame may be via calk, glue, adhesive and the like. Securing of the membrane frame, if used, to the case may be via calk, glue, grease, adhesive, screws or other fasteners, clips, press-fit, clamps, magnets, and the like, in any combination. One purpose of the optional membrane frame is to hold the shape of the membrane uniform, such as substantially planer, with optional consistent sag in the compliance area, such that compliance of the membrane during weighing is minimal, linear or consistent (in any combination) so as to not adversely affect the weighing function of the scale. Scale calibration may then inherently take into account any action of the membrane on motion or pressure of the weighing platform relative to the case. A seal 76 between the membrane and the case is shown.

A side view of a rigid penetrating element 83 is shown. The purpose of this element is to transfer weight or pressure from the weighing platform 86, through the membrane 75, to the weighing sensor 78. Any number of intermediate or mechanically connecting elements may be in this weight-path. The rigidity required is sufficient for the function of the scale. Note in particular that the rigidity may be only in the vertical axis. For example, a point, a sliding connection, or horizontally compliance may be used, permitting one or more horizontal motions or rotational motions of the weighing platform relative to the weighing element. The penetrating element may be metal or plastic, similar to the material of the case. However, the penetrating element does not need to be chew resistant, except for any portion that penetrates the weighing platform and is not otherwise protected. In addition, the penetrating element may be solely or partially electrical connectors or their shells, although such weight-bearing or penetration functions are not typically a primary function of electrical connectors in the art. The penetrating element may be solely or partially circuit boards. The penetrating element may be solely or partially a screw, bolt or rod, hollow or solid. Sealing of the penetrating element where it meets the membrane may be accomplished similarly to sealing as described above for the membrane to the case. Reinforcement may be provided within or around the penetration area.

The weight sensor 78 may be a load cell or other weight or pressure sensing device or assembly. Its output may be electrical, electronic, digital or analog, or optical. A hollow interior of a load cell is shown 77. A load cell's a free end, not shown, is typically connected directly or indirectly 81 to the penetrating element 83; while a fixed end, not shown, is connected directly or indirectly to the case 82. Note that such indirect connections may include the use of a circuit board, not shown.

Lower electronics 80 are in the case 82 and sealed against pathogens by the membrane 75 and membrane seals such 76. Immersion sterilizing fluid, such as could be used to sterilize the outside of the case, is often corrosive to electronic components and therefore such components should be protected from the immersion sterilizing fluid. Electronics include an interface to receive signals from the load cell or other weight sensor 78, interface to the wireless component(s) 73 in the upper module 86; a processor; non-transitory memory for both firmware and data, not shown explicitly; and a power source, such as rechargeable lithium batteries, not shown explicitly. These are well known in the art.

Upper electronics 73 are in the upper module 86. These provide an interface between the electronics 80 in the lower module and the wireless communication elements 87. The upper module includes a mating connector 71 comprising electrical contacts 72 to mate with the electrical contact points 84 in the penetrating element 83. Such mating is shown by arrows 85. The wireless communication element(s) 87 may be an antenna(s), such as a patch antenna, or a near-field antenna, or optical transmitter(s) or transceiver(s). If optical, ideally the optical element is redundant (not shown) so that if an animal being weighed is covering one element, communication is preserved by use of the redundant element. Ideally, redundant optical elements are spaced so that an animal is unlikely to cover both elements at the same time, such as by placing the elements proximal to different corners of the upper module or by spacing them more than the average or maximum diameter, width or length of an animal being weighed.

Either optical elements 87 or radio elements should have a narrow beam angle upward to communicate to electronics located above the top of a cage housing the scale. In a vivarium, cages are typically closely spaced so it is necessary to prevent communication interference between cages. Therefore, a upward facing beam angle in the range of 5 to 120 degrees, 10 to 120 degrees or 15 to 90 degrees is desired. It is also desirable to have the power outside of the such beam angle to be at least −3 db, −6 db, −12 db, −20 db, −30 db, or −40 db below the power in the such beam angle. An antenna may be a near-field antenna, configured with B field facing primarily vertical or upward to avoid interference with nearby cages.

A radio-receiving element may be defined at a height of 10 to 36 cm above the top of the upper module and directly above the center of the upper module 86 within 15, 30 or 45 degrees. A transmitting antenna in the upper module should have its power not reaching such a receiving element at least −3 db, −6 db, −12 db, −20 db, −30 db, or −40 db below the power reaching that receiving element. An antenna may broadcast signals balanced between B and E fields, or may be primarily a B field or an E field antenna. B field antennas have the advantage that they provide good near-field gain that drops off rapidly with distance preventing interference with nearby cages. An antenna may be a pad or loop, for example.

The upper module 86 may be removable from the lower module (82 with attached elements) by disconnecting the connector 71 from the connector 83. These two connectors, 71 and 83 also provide a weight path from the weighing platform 70 to the weight sensor 78. Multiple connectors providing multiple weight paths to a single or multiple (not shown) weight sensors may be used. Multiple connection points between the upper module and lower module may have the advantage of minimizing upper element or weighing platform tip or distortion.

A seal between one or more penetrating elements 83 and the membrane 75 is shown 79. Seal material may be similar to or dissimilar to the seal material 76 used between the membrane 75 and the case 82. Note that as shown 83 is both the penetrating element and a connector as part of the lower module.

Figure 2:
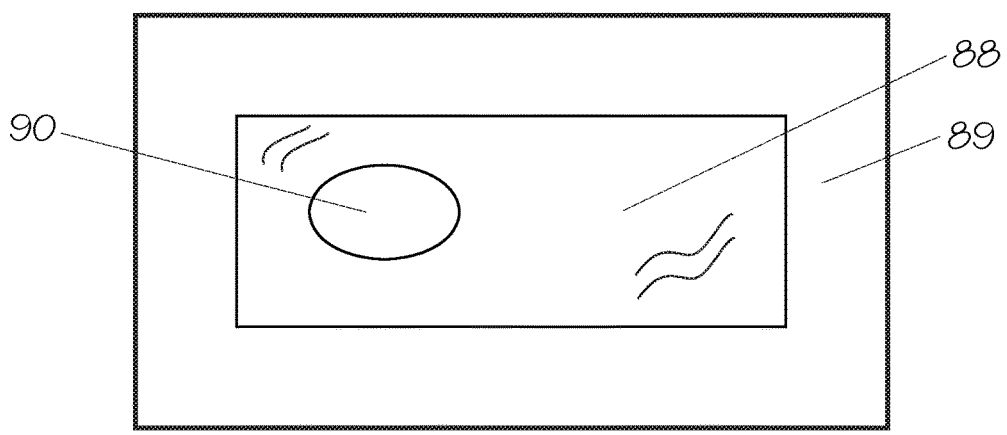
FIG. 2 shows a top view of areas in a flexible, exemplary compliant membrane.

Turning now to FIG. 2, we see an exemplary and overhead view of a planer compliant membrane. This view may be either scale realistic or schematic only. A perimeter area 89 is shown where an optional membrane frame (not shown) connects to the membrane (FIG. 1, 75, and all of FIG. 2). A penetration area or zone 90 is shown, through which the penetration element (FIG. 1, 83) passes. Although the borders between these areas are shown by hard lines in the Figure, such borders may not be so well defined. The penetration area may be created by the penetrating element and optionally its seal (FIG. 1, 79) or reinforcement (not shown). The compliance area 88 should isolate the perimeter area 89 from the penetration area 90 to permit the weighing platform 86 to have free motion, restricted only by the compliance zone of the membrane, with respect to the case 82, as described elsewhere herein.

A nexus of embodiments is a membrane 75 that provides both a seal of the case 82 and its contents to preserve sterility of the interior 93 of the lower module and flexibility to permit the motion or pressure of the upper module 86 to be transferred functional to one or more weight sensors, 78. Ideally, such compliance is both consistent and linear with weight.

Embodiments include more than one penetration element 83 and optionally more than one penetration area 90 of the membrane 75. For example, two or three penetration elements may be used to minimize tilt or distortion of the upper module 86 or the weighing platform surface 70. In some embodiments connections between two, three or more penetration elements to the weighing platform are rigid only or predominantly in the vertical axis, in order to permit bend, manufacturing or operational tolerances in other axes and planes. Such a vertical-axis-specific rigid connection may be the tip of a screw or other element where the upper module rests via gravity on three or more of these supporting elements.

Elements connected to or part of the case to accomplish positional alignment within a cage include protruding pins, recesses or detents, concave corners, or protruding curved, hooked, or triangular projections. Such projections, recesses or detents may mate with corresponding features in a cage or other scale receptacle such that the scale may be placed and removed by simple vertical motion by hand. Curved, hooked, or triangular projections may be used to place a scale in a receptacle by first aligning the projection(s), and then rotating the scale into a horizontal position so the projection(s) engage. Such elements are not shown in FIG. 1.

A nexus of novelty is the use of the compliant membrane to accomplish both pathogenic sterility and compliance for weight bearing penetration. Another nexus is the use of a single penetration. Another nexus is the use of a combined mechanical weight-bearing penetration and electrical penetration element. Another nexus is the use of electronics in both the upper and lower modules that connect electrically via the penetration element. Another nexus is the configuration of the skirt to minimize detritus from moving upward through the skirt-case gap onto the membrane, while permitting free, unimpeded motion, constrained only by a compliance zone of the membrane, for weighing. Another nexus is the easy removal of the weighing platform weighing platform from the case to permit separate sterilization by immersion in a sterilizing fluid of both the upper and lower module. Another nexus is the use of a connector integrated with the penetrating element that provides two additional functions: electrical connectivity between the case and lit of wireless communication and an electrical charging port for a power source in the case. Another nexus is the use of one or more electrical connectors as the rigid element as described herein. Another nexus is the use of flexible membrane with three separate purpose areas as defined herein. Another nexus is the use of upward facing, narrow-beam optical or radio wireless communication elements in the upper module.

Yet another nexus is the use of wireless communications that are free of any protocol that requires establishing an ID-specific association between the scale and a receiver. This limitation permits any scale to be placed in any cage without having to first perform, manually or automatically, and association step. It also avoids the possibility of a scale in one cage associating with a receiver for a different cage. Such a result could invalidate an entire study.

Suitable horizontal dimensions for the scale may be in the range of 2 to 24 inches, or the range of 4 to 10 inches. Ideally, the scale is sized so that one animal to be weighed may easily position itself fully on the scale. Suitable corner radii of the scale case and weighing platform should be large enough to prevent or minimize chewing, or be made out of a chew-resistant material, or both. A suitable gap between the weighing platform and the case is in the range of 1/64 to 1/2 inch, or in the range of 1/8 to 1/4 inch. The gap should be sized relative to the detritus or bedding in the cage. A suitable height for the overlap of the skirt over the case is in the range of 1/16 to 4 inches, or in the range of 1/8 to 2 inches. A suitable thickness of the membrane is in the range of 0.1 to 1.5 mm, or in the range of 0.2 to 0.8 mm. A suitable material for the membrane is neoprene, rubber or latex. Thickness should ideally depend on the desired weight range of the scale.

A scale of an embodiment is suitable for use in, or used in, a sterile animal cage that is free of electrical penetrations.

A scale of an embodiment may be used for any purpose other than weighing animals, particularly in environment where sterility is important, including for people, infants, organs, use for biological or chemical research, hazardous material, explosion-proof environments, corrosive environments, radioactive environments, or for other medical or research use.

Although "sterile" and "sterilizing" are used in the disclosure of this invention, these words may also mean "clean" and "cleaning," particularly with respect to undesirable material or contamination, such as dust, liquids, chemicals and the like.

One embodiment uses IR (infrared) transmitters, which may also be transceivers. The IR communications may be through an IR transparent top of the animal cage. The IR optical path may be restricted with tubes or lenses to restrict the amount of stray IR light, which might comprise IR-sensitive cameras. The IR spectrum may be restricted to an IR range for which cameras are not sensitive. The IR communication may be modulated such that lower power is needed, so that this IR light is dim enough to not interfere with cameras.

One embodiment only transmits weight values when it receives wirelessly a command to do so.

One embodiment only transmits weight values when the weight on the scale changes more than a predetermined amount: absolute or relative change; increased or decreased weight. A series of weights may pass through a smoothing or averaging function prior to transmission. Such a function may minimize sudden apparent changes in weight to movement of the animal being weighed. This function maybe used in the data path for weight value transmissions, or may be used in the data path to detect a change of weight that triggers a new transmission, or both.

One embodiment transmits a first series of weight values during a first time interval, at a first time spacing between values; then, transmit a second series of weight values during a second time interval, at a second time spacing between values. For example, weighs may be transmitted at eight samples/sec for two seconds, then at one sample per second for ten seconds.

One embodiment uses the transmitted scale weight in conjunction with an animal ID sensor. Such an animal ID sensor may be RF ID, capacitive using the top module, ECG electrical contacts on the top of the upper modules, or one or more camera images. If RFID is used, an RFID chip may be on the animals' ear; the RFID receiver may be in the scale or outside the animal cage. Numerous other forms of animal ID are known in the art.

One embodiment comprises one or more IR transceivers in the upper module, facing upward. IR transmissions to and from these transceivers may be through a transparent cage top. Many other forms and configurations of wireless communication are known in the art.

One embodiment of a system of measurement and a method of measurement uses the sterile, wireless scale in an animal cage that uses an animal ID to associate and record weights on the scale with specific animals in a cage with more than animal.

One embodiment comprises one or more optical communication elements on the top of the lid that are elevated above the top of the lid so as to avoid optically interfering contamination, such as bedding.

One embodiment comprises one or more communication elements comprising a narrow beam angle so as to avoid interference with other cage or cage-associated communication elements.

One embodiment comprises a communication protocol free of device-ID specific association or device pairing. One embodiment comprises a communication protocol free of device-ID.

One embodiment comprises a case with at least one corner partially cut off or comprises a concave recess, or both, so as to mate with a curved inside corner of a cage.

Certain best modes or implementation notes, or elements of embodiments, are listed below:

(a) The spring pressure from the membrane should be minor and may be ignored or corrected for during calibration. With no weight on the weighing platform, the membrane may sag and thus generate an artificial weight. With some weight on the weighing platform, the membrane may be stretched and thus generate an upward force appearing as a negative weight.

(b) Scales should be calibrated at two points: a zero (tare weight) and at a nominal weight, such as an average weight of an expected load (e.g., a mouse or rat), or 10%, 25% or 50% of full scale. Such calibration assumes sufficient linearity and effectively generates an offset and slope of the weight v. voltage curve.

(c) Any twist or non-uniformity of the membrane may produce strange, inconsistent or non-linear forces. Thus, design, manufacturing and embodiments should strive to minimize any distortion, twisting, asymmetry, or non-uniformity of the membrane.

(d) The membrane may also be called a gasket, depending on context and what function or attribute of the membrane is being discussed.

A mouse typically weights about 25 grams. A rat weighs typically 200 to 500 grams. A scale with full-scale range of 1000 grams may be suitable for both mice and rats.

(e) Embodiments include limit stops for the upper module, which may be fixed height relative to the case or may be adjustable, such as screws or set screws.

(f) Lithium batteries may run 1 to 4 weeks between charging. Embodiments include charring through the same connector on the lower module that is used to connect to the upper module. Also embodiments include entering calibration data through this same connector. Embodiments include calibration (setting and storing calibration coefficient) via the communication port. Embodiments include no calibration parameters or coefficients stored in the scale but rather these are kept external, so that correcting raw scale data is done externally after the scale transmits scale weight as raw data. Embodiments include limit testing prior to transmission; storing, averaging and queuing of weight data.

(g) Steps in order used to recycle scales between cages and studies: separate upper and lower modules; clean both; charge lower module; sterilize both; then reassemble.

All embodiment and combinations may be used in a vivarium.

Embodiments are specifically claimed for a vivarium that uses a scale as described in the specification, claims or drawings. Embodiments are specifically claimed for a method of operating a vivarium that uses a scale as described in the specification, claims or drawings.

Definitions

Value of a weight—a digital or analog weight, number, value, n-tuple, or a metric that can be used to compute a weight, or a metric derived from a weight. As one example, a simple digital reading from an analog-to-digital (A/D) converter that reads a voltage from a strain gauge or load cell may be a "value of a weight." As the k-factor of the strain gauge is known, as are other fixed constants and linear factors, the weight on the scale is easily computed from this value. In some contexts, a "weight" refers to this value of a weight.

Fixed—when two or more elements are fixed or affixed to each other, there may be or may not be intervening elements, such as spacers, rods, arms, washers and the like. So long as the two elements and the embodiment operate as if they are fixed, and they are effectively so mechanically coupled, the fixing is equivalent.

Electrically connected—when two or more elements are electrically or electronically connected to each other, or adapted to be so connected, there may be or may not be intervening electrical or electronic elements, including but not limited to processors, filters, communication links and the like. So long as the two elements and the embodiment operate as if they are electrically or electronically connected, and they are effectively so connected, the connecting is equivalent. Note the intervening elements may change the form, timing, filtering or aggregation of the signals or data; however, so long as data exiting the connection is responsive to the data entering the connection the connection is equivalent for the purposes of an embodiment or claim.

Communications element—one or more electronic components that send, receive or both, digital or analog data. Methods used include but are not limited to IR light, UV light, visible light, audio, sub-audio, ultrasonic, wireless, near-field or far-field radio, haptic, or other electromagnet communications.

Mechanically coupled or operatively mechanically coupled—transfer weight, motion or pressure from one element to another via the mechanical coupling or operative mechanical coupling. This describes a specific structural element or operation of a specific structural element, not a "functional element" in a claim. As one example, transfer points refers to a structural element, not a functional element. Such structural v. functional applies to claim construction. "Operative" means such that the scale functions as intended. One embodiment mechanically couples from a weighing surface to the free ends of one or more load cells to effectively transfer the weight on the weighing surface to the free ends of the one or more load cells.

Fluid—such as a sterilizing fluid, may be a liquid, a gas, or an aerosol.

Free of rigid attachment—means the upper module is able to move or transmit weight as motion or as pressure to the lower module. It may sit on or pass through a flexible membrane, or another flexible support, such as rubber pads, hinges, scissors support, or other compliant coupling.

Pathogen-free—means the population of microbes, including but not limited to bacteria, viruses, prions and toxins, relevant to the experiment, are sufficiently reduced to meet the needs of the study, or to not impact the health, performance or behavior of the target animal population or of the workers.

Sterile—pathogen-free. Note that "sterile" may refer to one volumetric area compared to another and may refer only to problematic pathogens, depending on a study, study animals, and safety considerations.

Sealed enclosure—an enclosure sealed against pathogens that impact or alter study results, or alter the credibility or repeatability of study results, entering or leaving the enclosure.

Transmit difference threshold—may be a percentage of weight, or an absolute weight, or a formula incorporating both the percentage and absolute values.

Ideal, Ideally, Optimum and Preferred—Use of the words, "ideal," "ideally," "optimum," "optimum," "should" and "preferred," when used in the context of describing this invention, refer specifically a best mode for one or more embodiments for one or more applications of this invention. Such best modes are non-limiting, and may not be the best mode for all embodiments, applications, or implementation technologies, as one trained in the art will appreciate.

All examples are sample embodiments. In particular, the phrase "invention" should be interpreted under all conditions to mean, "an embodiment of this invention." Examples, scenarios, and drawings are non-limiting. The only limitations of this invention are in the claims.

May, Could, Option, Mode, Alternative and Feature—Use of the words, "may," "could," "option," "optional," "mode," "alternative," "typical," "ideal," and "feature," when used in the context of describing this invention, refer specifically to various embodiments of this invention. Described benefits refer only to those embodiments that provide that benefit. All descriptions herein are non-limiting, as one trained in the art appreciates.

All numerical ranges in the specification are non-limiting examples only.

Embodiments of this invention explicitly include all combinations and sub-combinations of all features, elements and limitation of all claims. Embodiments of this invention explicitly include all combinations and sub-combinations of all features, elements, examples, embodiments, tables, values, ranges, and drawings in the specification and drawings. Embodiments of this invention explicitly include devices and systems to implement any combination of all methods described in the claims, specification and drawings. Embodiments of the methods of invention explicitly include all combinations of dependent method claim steps, in any functional order. Embodiments of the methods of invention explicitly include, when referencing any device claim, a substation thereof to any and all other device claims, including all combinations of elements in device claims.

The invention claimed is:

1. A wireless weighing scale comprising:
   a case comprising an interior comprising interior electronics comprising a weight sensor;
   a weighing platform comprising: platform electronics, a platform electrical connector, and an optical communication port;
   a flexible membrane comprising a perimeter fixed zone, a central penetration zone, and a compliance zone; wherein the compliance zone isolates the fixed zone from the penetration zone;
   wherein the flexible membrane perimeter fixed zone is attached to a respective perimeter portion of the case, defining a lower surface of the flexible membrane facing the interior of the case, and an opposing upper surface of the flexible membrane; wherein the attachment comprises a sterile seal;
   a penetrating fastener, wherein the penetrating fastener penetrates the penetration zone of the flexible membrane, wherein the penetration is sterile sealed; and
   wherein an upper end of the penetrating fastener is above the flexible membrane and a bottom end of the penetrating fastener is below the flexible membrane;
   wherein the penetrating fastener comprises upper electrical contact points above the flexible membrane and lower electrical contact points below the flexible membrane, and wherein at least two of the upper electrical contact points are electrically connected to respective at least two of the lower electrical contact points;
   a sterile volume, defined by the interior of the case and the lower surface of the flexible membrane;

wherein the upper end of the penetrating fastener is adapted to removably mechanically mate with the weighing platform;

wherein the upper electrical contact points are adapted to removably electrically mate with the platform electrical connector;

wherein the lower electrical contact points are adapted to electrically mate to the interior electronics; and wherein the scale is adapted to transmit a value of a weight on the weighing platform, the weight mechanically coupled from the weighing platform through the penetrating fastener to the weight sensor, via the optical communication port.

2. The weighing scale of claim 1 wherein:
an exterior of the case, the upper surface of the flexible membrane, and an upper portion of the penetrating fastener above the flexible membrane, together form an exterior of a primary module of the scale; and
wherein the primary module and the weighing platform are adapted to be separately sterilized by submersion in a sterilizing fluid.

3. The weighing scale of claim 1 wherein:
the weighing platform comprises a platform skirt, adapted such that when the weighing platform is removably mated with an upper portion of the penetrating fastener above the flexible membrane, the platform skirt surrounds and overlaps an upper perimeter of the case such that the weighing platform forms a drip-proof covering over the upper surface of the membrane and the upper end of the penetrating fastener.

4. The weighing scale of claim 1 further comprising:
two bi-directional optical communication ports;
wherein the two bi-directional optical communication ports are spaced at least an average diameter of a moving study animal.

5. The weighing scale of claim 1 wherein:
the scale transmits weight responsive to a command received via the optical communication port.

6. The weighing scale of claim 1 wherein:
the optical communication port comprises an optical communication cone angle of 45 degrees or less.

7. The weighing scale of claim 1 wherein:
the weighing scale is adapted to pass weight through a weight bearing path: from a study animal on a top of the weighing platform, through the weighing platform, then through penetrating fastener, then through the weight sensor, then to the case, wherein the weight bearing path comprises any necessary rigid linkages to complete the weight bearing path.

8. The weighing scale of claim 1 wherein:
the weighing scale is adapted to pass an electronic weight value through an electrical path: from the weight sensor, through the interior electronics, through the lower electrical contact points, through the respectively connected upper electrical contact points, through the platform electrical connector, through the platform electronics, to the optical communication port, and then the electronic weight value is transmitted optically from the optical communication port.

9. The weighing scale of claim 1 wherein:
the wireless communication port comprises a protocol, transmitting weight data, that is free of device ID specific association with another communicating device.

10. The weighing scale of claim 1 wherein:
the wireless communication port comprises a protocol, transmitting weight data, that is free of a specific device ID in each transmitted packet.

11. The weighing scale of claim 10 wherein:
the weighing scale is in a vivarium comprising at least 100 cages.

12. A method of weighing a study animal comprising the steps:
waiting for a study animal to be on weighing platform of weighing scale;
transmitting wirelessly a weight of the study animal using the weighing scale
wherein the weighing scale comprises:
a case comprising an interior comprising interior electronics comprising a weight sensor;
a weighing platform comprising: platform electronics, a platform electrical connector, and an optical communication port;
a flexible membrane comprising a perimeter fixed zone, a central penetration zone, and a compliance zone; wherein the compliance zone isolates the fixed zone from the penetration zone;
wherein the flexible membrane perimeter fixed zone is attached to a respective perimeter portion of the case, defining a lower surface of the flexible membrane facing the interior of the case, and an opposing upper surface of the flexible membrane; wherein the attachment comprises a sterile seal;
a penetrating fastener, wherein the penetrating fastener penetrates the penetration zone of the flexible membrane, wherein the penetration is sterile sealed; and
wherein an upper end of the penetrating fastener is above the flexible membrane and a bottom end of the penetrating fastener is below the flexible membrane;
wherein the penetrating fastener comprises upper electrical contact points above the flexible membrane and lower electrical contact points below the flexible membrane, and wherein at least two of the upper electrical contact points are electrically connected to respective at least two of the lower electrical contact points;
a sterile volume, defined by the interior of the case and the lower surface of the flexible membrane;
wherein the upper end of the penetrating fastener is adapted to removably mechanically mate with the weighing platform;
wherein the upper electrical contact points are adapted to removably electrically mate with the platform electrical connector;
wherein the lower electrical contact points are adapted to electrically mate to the interior electronics; and
wherein the weighing scale is adapted to transmit a value of a weight on the weighing platform, the weight mechanically coupled from the weighing platform through the penetrating fastener to the weight sensor, via the optical communication port.

13. A method of sterilizing wireless weighing scale wherein:
the wireless weighing scale comprises:
a case comprising an interior comprising interior electronics comprising a weight sensor;
a weighing platform comprising: platform electronics, a platform electrical connector, and an optical communication port;
a flexible membrane comprising a perimeter fixed zone, a central penetration zone, and a compliance zone; wherein the compliance zone isolates the fixed zone from the penetration zone;

wherein the flexible membrane perimeter fixed zone is attached to a respective perimeter portion of the case, defining a lower surface of the flexible membrane facing the interior of the case, and an opposing upper surface of the flexible membrane; wherein the attachment comprises a sterile seal;

a penetrating fastener, wherein the penetrating fastener penetrates the penetration zone of the flexible membrane, wherein the penetration is sterile sealed; and wherein an upper end of the penetrating fastener is above the flexible membrane and a bottom end of the penetrating fastener is below the flexible membrane;

wherein the penetrating fastener comprises upper electrical contact points above the flexible membrane and lower electrical contact points below the flexible membrane, and wherein at least two of the upper electrical contact points are electrically connected to respective at least two of the lower electrical contact points;

a sterile volume, defined by the interior of the case and the lower surface of the flexible membrane;

wherein the upper end of the penetrating fastener is adapted to removably mechanically mate with the weighing platform;

wherein the upper electrical contact points are adapted to removably electrically mate with the platform electrical connector;

wherein the lower electrical contact points are adapted to electrically mate to the interior electronics; and wherein the weighing scale is adapted to transmit a value of a weight on the weighing platform, the weight mechanically coupled from the weighing platform through the penetrating fastener to the weight sensor, via the optical communication port; and the method comprises the steps:

disassembling the weighing platform from the upper end of the penetrating fastener;

sterilizing the weighing platform and the case separately by submerging each in a sterilizing fluid;

reassembling the weighing platform with the upper end of the penetrating fastener.

\* \* \* \* \*